US011138864B2

(12) United States Patent
Rhee et al.

(10) Patent No.: US 11,138,864 B2
(45) Date of Patent: *Oct. 5, 2021

(54) EARLY ALERT SYSTEM FOR LIVESTOCK DISEASE DETECTION WITH A FEEDLOT FENCE CROSSBAR-EMBEDDED RFID ANTENNA

(71) Applicant: Hana Micron America Inc., Milpitas, CA (US)

(72) Inventors: Seungwhan Rhee, Milpitas, CA (US); Songtao Jin, Milpitas, CA (US); Sung Bok Kwak, Milpitas, CA (US)

(73) Assignee: HANA MICRON INC., Asan-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/848,055

(22) Filed: Mar. 20, 2013

(65) Prior Publication Data

US 2013/0222141 A1    Aug. 29, 2013

Related U.S. Application Data

(63) Continuation-in-part of application No. 13/166,520, filed on Jun. 22, 2011.

(51) Int. Cl.
*G08B 23/00* (2006.01)
*G06Q 10/08* (2012.01)
*G06Q 50/02* (2012.01)
*G06F 19/00* (2018.01)

(52) U.S. Cl.
CPC ......... *G08B 23/00* (2013.01); *G06F 19/3418* (2013.01); *G06F 19/3493* (2013.01); *G06Q 10/0833* (2013.01); *G06Q 50/02* (2013.01)

(58) Field of Classification Search
CPC .... A01K 11/006; A01K 11/004; G06Q 50/02; G06Q 50/24; G06Q 10/0833; G06Q 10/24
USPC .............................. 340/539.12, 573.1, 573.2
See application file for complete search history.

(56) References Cited

U.S. PATENT DOCUMENTS

| | | | |
|---|---|---|---|
| 3,370,296 A * | 2/1968 | Greenberg | 346/14 R |
| 6,411,213 B1 * | 6/2002 | Vega et al. | 340/573.3 |
| 7,543,549 B2 * | 6/2009 | Valencia et al. | 119/174 |
| 8,185,101 B1 * | 5/2012 | Wiseman et al. | 455/422.1 |
| 8,307,785 B2 * | 11/2012 | Zimmerman et al. | 119/51.02 |
| 2004/0116821 A1 * | 6/2004 | Beiswenger | G06F 19/3493 600/549 |

(Continued)

*Primary Examiner* — Jennifer Mehmood
*Assistant Examiner* — Omar Casillashernandez
(74) *Attorney, Agent, or Firm* — Sughrue Mion, PLLC

(57) ABSTRACT

An early alert system and a method for livestock disease detection are disclosed. An activity measurement zone (AMZ) is defined near an incentive device (e.g. a livestock feeder) with an RFID tag reader and a uniquely-designed feedlot fence crossbar-embedded RFID antenna, which amplifies multiple signal wavelengths in a single dipole antenna. The early alert system is configured to detect and count an animal's access into the AMZ with an RFID tag attached to the animal. If the animals' activity relative to the AMZ drops to an alarmingly low level (e.g. dropping below an alert trigger point) over time, then a user of the early alert system is informed of a potential health problem of the animal and may also be encouraged to inspect the animal in person for further determination of its current health and potential medical issues.

12 Claims, 11 Drawing Sheets

(56) References Cited

U.S. PATENT DOCUMENTS

| | | | | |
|---|---|---|---|---|
| 2005/0012623 | A1* | 1/2005 | Jackson et al. | 340/573.3 |
| 2007/0288249 | A1* | 12/2007 | Rowe et al. | 705/1 |
| 2008/0143620 | A1* | 6/2008 | Khatri | 343/726 |
| 2012/0012069 | A1* | 1/2012 | Hempstead et al. | 119/712 |
| 2012/0089340 | A1* | 4/2012 | Huisma | 702/19 |

* cited by examiner

An Implemented Example of an Electrical Outlet-Powered Early Alert System for Livestock Disease Detection with a Feedlot Fence Crossbar-Embedded Antenna

500

An Implemented Example of an Alternative Energy-Powered Early Alert System for Livestock Disease Detection with a Feedlot Fence Crossbar-Embedded Antenna

600

Example of characteristics of an epidemic among animals in a livestock housing

700

Example of an alert trigger point for livestock disease detection

800

| Tag ID | Type | DOB | Gender | Owner | Vaccine Records | AMZ Count | Other Info |
|---|---|---|---|---|---|---|---|
| A00001 | Premium | 7/17/2010 | F | KC Farms | | | |
| A00002 | Regular | 7/18/2010 | M | Joe's Co | | | |
| A00003 | Regular | 7/20/2010 | F | Joe's Co | | | |
| A00004 | Premium | 7/25/2010 | M | KC Farms | | | |

900

1000A

1000B

A system application flow diagram

An example of a reporting format for an Early Alert System for Livestock Disease Detection

1300

EARLY ALERT SYSTEM FOR LIVESTOCK DISEASE DETECTION WITH A FEEDLOT FENCE CROSSBAR-EMBEDDED RFID ANTENNA

BACKGROUND OF THE INVENTION

The present invention generally relates to animal-identifying electronic systems. More specifically, the present invention relates to one or more embodiments of a livestock feeder-zone radio frequency identification (RFID) system with a feedlot fence crossbar-embedded RFID antenna. The present invention also relates to one or more embodiments of an early alert system for livestock disease detection with an activity measurement zone (AMZ), which is defined by a data reading range of an RFID antenna. Furthermore, the present invention also relates to an early detection of a contagious disease in farm animals.

Livestock illness detection and control of contagious diseases and epidemics have become high-priority concerns in modern livestock farming industry. As farmers attempt to improve yield and efficiency of their livestock farms within available spaces, animals are often placed in space-constrained livestock housing and are highly susceptible to rapid contagion of dangerous epidemics. For example, avian influenza outbreaks in chicken farms, mad cow disease in cattle farms, and foot-and-mouth disease outbreaks in various farm animals have become more common and frequent in high-density farming environments. Early detection and proactive control of these outbreaks have become more difficult as space-constrained and dense livestock farming are likely causing even faster spread of the diseases among farm animals before any conventional quarantine and treatment measures can take effect.

The conventional measure of detecting a disease in farm animals is generally slow and cumbersome. Farmers have to manually monitor conditions of each farm animals, which are typically contained in a livestock housing. An animal suspected of being under the influence of a contagious disease is manually checked for its vital signs such as body temperature and heart rate. If this animal is confirmed to be infected of a dangerous or contagious disease, then it may be isolated from the flock for further treatment and handling. This conventional disease detection method is highly dependent on the level of experience and attention of a farmer monitoring the animals, thereby causing some serious medical conditions on a farm animal to be spread to other nearby animals before the manual inspection process takes place. Furthermore, the process of checking vital signs of an ill animal is a serialized, cumbersome, and slow process. This conventional checkup process frequently causes delay in expediting quarantine, prevention, and/or treatment procedures of remaining animals.

Because any delay in quarantine, prevention, and treatment procedures during an outbreak of a contagious disease in a livestock farm can cause rapid infections to remaining animals, investment losses, and increased health risks to humans, it is highly desirable to devise an early alert system and a method for livestock disease detection. Furthermore, it may also be advantageous to utilize RFID tags attachable to animals for a systematic management of early detection of diseases for farm animals. In addition, because conventional RFID antennas are not specifically designed to formulate RFID tag access ranges for monitoring animal health-related activities, it may also be beneficial to design an early alert system for livestock disease detection with a unique and durable RFID antenna that can be structurally embedded in a feedlot fence near a livestock feeder zone for defining and enabling a precise RFID tag reading range around the livestock feeder zone.

SUMMARY

Summary and Abstract summarize some aspects of the present invention. Simplifications or omissions may have been made to avoid obscuring the purpose of the Summary or the Abstract. These simplifications or omissions are not intended to limit the scope of the present invention.

In one embodiment of the invention, an early alert system for livestock disease detection is disclosed. This early alert system for livestock disease detection comprises: a feedlot fence crossbar-embedded RFID antenna attached to or incorporated into a feedlot fence crossbar near a livestock feeder; an activity measurement zone (AMZ) defined by an RFID signal projection from the feedlot fence crossbar-embedded RFID antenna operatively connected to an RFID tag reader, wherein the AMZ is further specified as a zone above or around the livestock feeder; the livestock feeder located near or inside the AMZ to encourage an animal attached with an RFID tag to enter and exit the AMZ periodically or frequently; the RFID tag reader configured to read from or write to the RFID tag attached to the animal if the animal is inside the AMZ defined by the RFID signal projection from the RFID antenna; a portable or fixed main controller unit configured to control, request data from, or send data to one or more elements of the early alert system using a wireless connection, a physical connection, or both; a power supply unit configured to supply and regulate electrical power to the feedlot fence crossbar-embedded RFID antenna, the RFID tag reader, and the portable or fixed main controller unit; a computer server with a CPU and a memory unit operatively connected to the RFID tag reader and the portable or fixed main controller unit to receive information from or transmit information to the RFID tag attached to the animal; and an analytical program module configured to set, adjust, detect, and/or use an alert trigger point for alerting a user that the animal requires personal attention for further medical inspection if an AMZ count for the animal over a period of time drops below the alert trigger point, wherein the analytical program module is executed on the CPU and the memory unit of the computer server, or at least partially executed on another CPU and another memory unit in the portable or fixed main controller unit.

In another embodiment of the invention, a method of alerting a potential livestock disease to a user of an early alert system with a feedlot fence crossbar-embedded RFID antenna is disclosed. This method comprises the steps of: powering a main controller unit, an RFID tag reader, and the feedlot fence crossbar-embedded RFID antenna of the early alert system by using a power supply unit of the early alert system; defining an activity measurement zone (AMZ) enabled by the RFID tag reader and the feedlot fence crossbar-embedded RFID antenna to be above or around a livestock feeder, wherein the feedlot fence crossbar-embedded RFID antenna is attached to or incorporated by a feedlot fence crossbar next to the livestock feeder; attaching an RFID tag to an animal, wherein the RFID tag reader can read from or write to the RFID tag if the RFID tag is within the AMZ; activating the early alert system for livestock disease detection; monitoring the frequency of the animal's entrance into the AMZ by accessing the RFID tag attached to the animal; and if an alert trigger point is reached, informing the user of the early alert system to encourage further inspection of the animal for a potential health problem or an infection.

DETAILED DESCRIPTION

Figure 1:
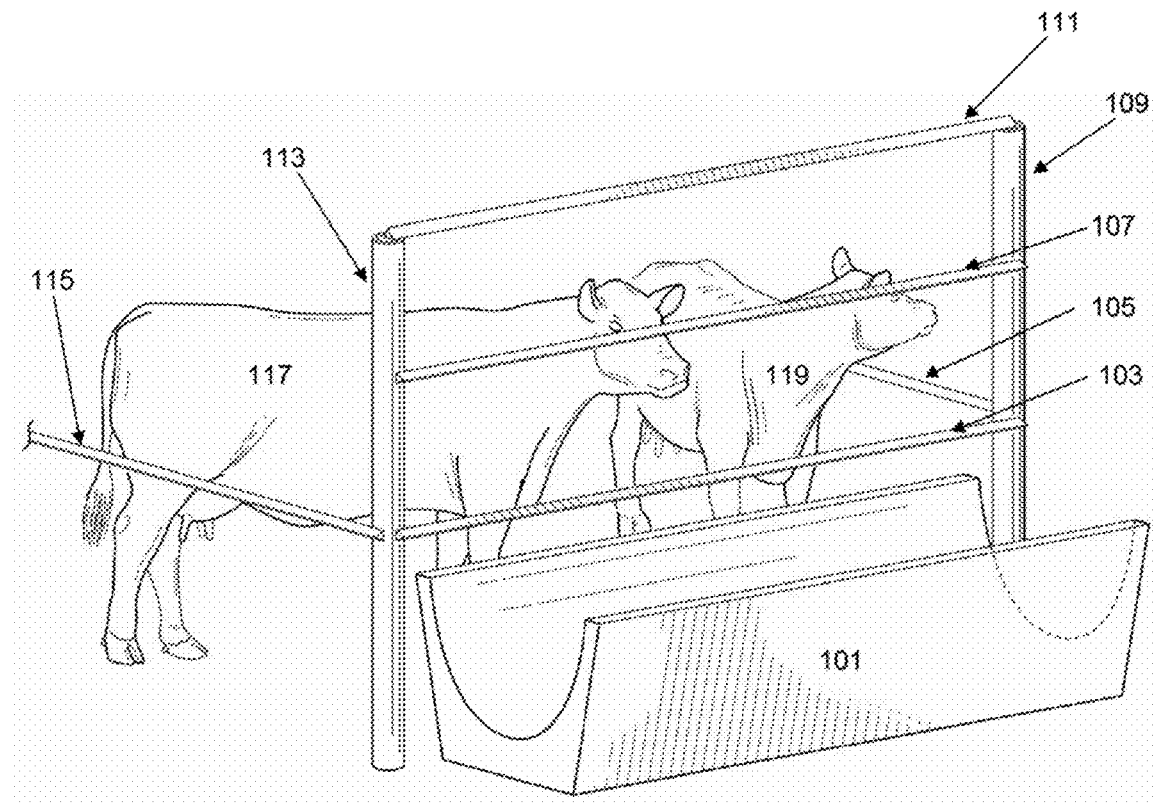
FIG. 1 shows a perspective view of a typical feedlot fence structure containing livestock animals.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

The detailed description is presented largely in terms of description of shapes, configurations, and/or other symbolic representations that directly or indirectly resemble an early alert system and a related method for livestock disease detection with a feedlot fence crossbar-embedded RFID antenna. These descriptions and representations are the means used by those experienced or skilled in the art to most effectively convey the substance of their work to others skilled in the art.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment. Furthermore, separate or alternative embodiments are not necessarily mutually exclusive of other embodiments. Moreover, the order of blocks in process flowcharts or diagrams representing one or more embodiments of the invention do not inherently indicate any particular order nor imply any limitations in the invention.

For the purpose of describing the invention, a term "livestock" is defined as farm animals raised for use and/or profit. The term "livestock" can include, but are not limited to, cattle, sheep, pigs, goats, horses, donkeys, mules, and poultry (e.g. chickens, ducks, turkeys, and geese).

Furthermore, for the purpose of describing the invention, a term "activity measurement zone" (AMZ) is defined as a designated area in which the entrance and/or the exit of a monitored animal into the designated area is counted and tracked by an RFID tag and an RFID reading device. In a preferred embodiment of the invention, the RFID reading device is operatively connected to or incorporated into a feedlot fence crossbar RFID antenna. Preferably, the RFID reading device is an RFID tag reader unit or another RFID tag access controlling unit, which is operatively connected to the feedlot fence crossbar RFID antenna. In the preferred embodiment of the invention, the feedlot fence crossbar RFID antenna has an RFID tag access range, which is custom-tuned to a perimeter above or around a livestock feeder, so that the activity measurement zone (AMZ) can be defined above or around the livestock feeder. In this particular preferred embodiment, the livestock feeder serves as an incentive device for the AMZ of the early alert system. Preferably, in one or more embodiments of the invention, each AMZ may be situated inside or near one or more incentive devices, which encourage an animal to enter the AMZ frequently or periodically.

In addition, for the purpose of describing the invention, a term "livestock feeder" is defined as a container, a bowl, a plate, or another animal feed-holding apparatus, which can be accessed by an animal to fetch animal feed and/or water.

Furthermore, for the purpose of describing the invention, a term "feedlot fence" or "feedlot fence structure" is defined as one or more bars, supports, and/or poles, which at least partially define and/or at least partially contain animals' freedom of movement. For example, a feedlot fence can prevent an animal from going over a particular demarcation or a boundary defined by livestock owners.

In addition, for the purpose of describing the invention, a term "feedlot fence crossbar" is defined as a horizontal bar, a diagonal bar, or another feedlot fence-related structure which is not entirely vertical in its orientation.

Furthermore, for the purpose of describing the invention, a term "feedlot fence crossbar-embedded," or a term "crossbar-embedded" is defined as "being attached to" or "being incorporated into" a crossbar used in a feedlot fence-related structure.

Moreover, for the purpose of describing the invention, a term "epidemic" and a term "contagious disease" are defined as an infectious disease for animals and/or humans, wherein the infectious disease may spread by physical contact, air, liquid, or another method of disease transmission.

In addition, for the purpose of describing the invention, a term "radio frequency identification," or RFID, is defined as a wireless signal-based identification of a wirelessly-accessible tag, called an "RFID tag" using a wirelessly-accessible tag reader, called "RFID tag reader." In general, an RFID tag contains information which may be written and/or read by the RFID tag reader, an RFID antenna operatively connected to the RFID tag reader, or another tag information access device. In a preferred embodiment of the invention, RFID operates in ultra high frequencies (UHF) to achieve longer read/write ranges (e.g. up to several meters) and multiple tag read/write capabilities, which were difficult to achieve in conventional low frequency (LF)-based RFID devices exhibiting shorter read/write ranges (e.g. approximately up to 30 centimeters) and single tag scan functionalities. In a preferred embodiment of the invention, the UHF range for the RFID tag reader is defined by ISO/IEC 18000-6 air interface standard, which utilizes an operating frequency range of 860 MHz~960 MHz. In another embodiment of the invention, the UHF operating frequency range may be defined more broadly as 300 MHz~3 GHz. In general, the conventional LF operating frequencies are below the UHF RFID tag reader operating frequency ranges.

Furthermore, for the purpose of describing the invention, a term "alternative energy source" is defined as an energy source which enables an electrical device to be at least not entirely dependent on a conventional electrical power line or an electrical outlet for powering the electrical device. In addition, a term "hybrid alternative energy sources" is defined as a plurality of energy sources which enable a powered device to be at least not entirely dependent on a conventional electrical power line or an electrical outlet. For example, a solar panel or a wind turbine may be called an "alternative energy source." A combination of one or more solar panels and wind turbines to power an electrical device may be called "hybrid alternative energy sources."

In addition, for the purpose of describing the invention, a term "hybrid charge controller" is defined as an electrical controller and/or an integrated electrical unit that controls, converts, and/or regulates electrical voltage and currents from one or more alternative energy sources for charging a rechargeable battery unit.

One aspect of an embodiment of the present invention is providing an early alert system for livestock disease detection using RFID technology with a feedlot fence crossbar-embedded RFID antenna.

Another aspect of an embodiment of the present invention is providing a method of early detection of livestock disease using RFID technology with a feedlot fence crossbar-embedded RFID antenna.

Yet another aspect of an embodiment of the present invention is utilizing a novel concept of an activity measurement zone (AMZ) in conjunction with a feedlot fence crossbar-embedded RFID antenna and a livestock feeder as an incentive device for early detection of livestock disease.

In addition, another aspect of an embodiment of the present invention is providing a motivation, an incentive, or an encouragement for an animal to enter the activity measurement zone (AMZ) frequently or periodically by situating a livestock feeder, a water feed system, or another incentive device near or inside the activity measurement zone (AMZ).

Furthermore, one aspect of an embodiment of the present invention is providing an early alert system with a feedlot fence crossbar-embedded RFID antenna and a related method for livestock disease detection, which are powered by hybrid alternative energy sources.

Another aspect of an embodiment of the present invention is providing an early alert system and a related method of early detection of livestock disease using RFID technology, hybrid alternative energy sources, a portable main controller unit, a feedlot fence crossbar-embedded RFID antenna, a network attached storage, a cellular network, and application programs.

FIG. 1 shows a perspective view of a typical feedlot fence structure (100) containing livestock animals (117, 119). A feedlot fence structure (100) near a livestock feeder (101) typically comprises a first vertical fence support (113), a second vertical fence support (109), and one or more feedlot fence crossbars (103, 107, 111). In the feedlot fence structure (100) as shown in FIG. 1, there are three feedlot fence crossbars (103, 107, 111), which generally serve the function of preventing the livestock animals (117, 119) from going through or jumping over the feedlot fence structure (100).

Some feedlot fence structures, such as the feedlot fence structure (100) shown in FIG. 1, additionally includes one or more side fence bars (115, 105) to further contain livestock animals' sideways movement. Other feedlot fence structures may not include any side fence bars. Furthermore, as shown in FIG. 1, the livestock animals (117, 119) contained in the feedlot fence structure may be cattle, and the livestock feeder (101) may contain cattle feed. In another example, the livestock animals may be pigs, chickens, ducks, or any other livestock animals with corresponding livestock feed contained in the livestock feeder (101).

Figure 2:
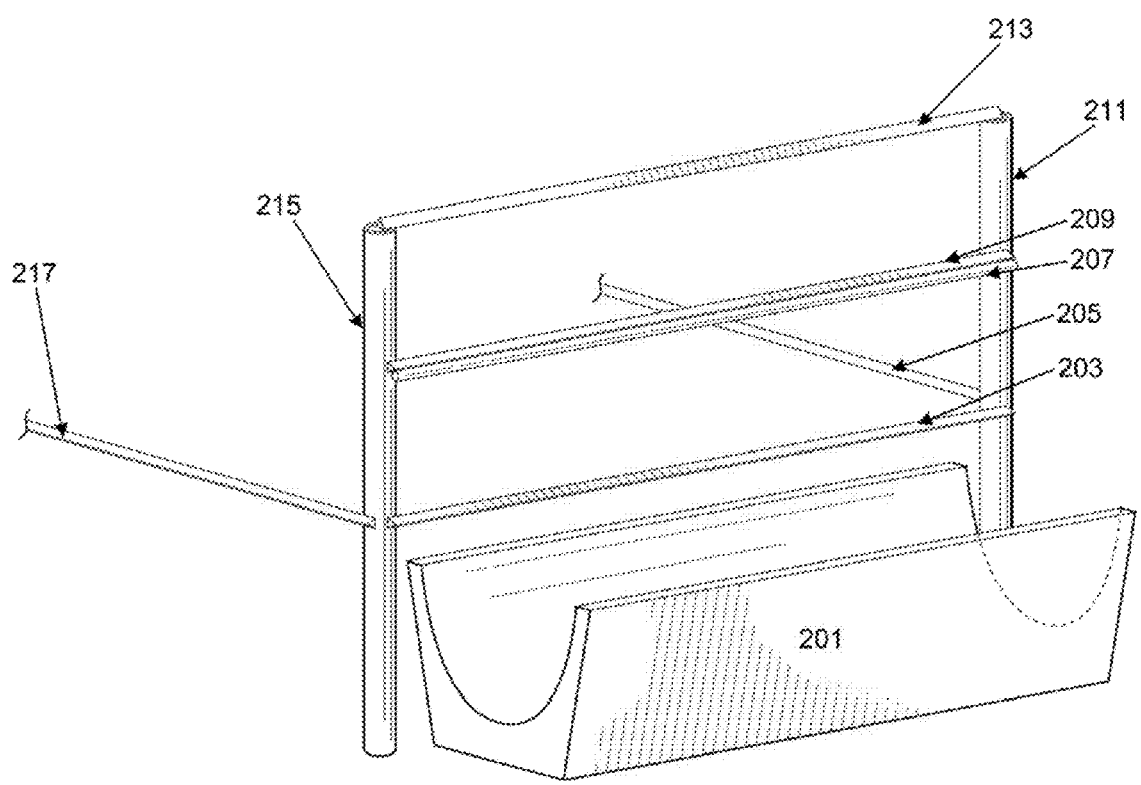
FIG. 2 shows a perspective view of a feedlot fence crossbar-embedded RFID antenna for an early alert system for livestock disease detection, in accordance with an embodiment of the invention.

FIG. 2 shows a perspective view of a feedlot fence crossbar-embedded RFID antenna (207) in a feedlot fence structure (200) for an early alert system for livestock disease detection, in accordance with an embodiment of the invention. In a preferred embodiment of the invention, the feedlot fence crossbar-embedded RFID antenna (207) is a multiple-wavelength dipole antenna that can effectively produce an intended RFID tag access range (e.g. 319 of FIG. 3) without requiring multiple half-wavelength dipole antennas within the feedlot fence crossbar-embedded RFID antenna (207). In another embodiment of the invention, the feedlot fence crossbar-embedded RFID antenna (207) is one or more discrete half-wavelength dipole antennas, which may produce higher signal-amplification efficiencies than the multiple-wavelength dipole antenna. In one example, the feedlot fence crossbar-embedded RFID antenna (207) is approximately 10~12 feet in length and 1~2 inches in diameter. In another example, the feedlot fence crossbar-embedded RFID antenna (207) exhibits other dimensions that are appropriately sized for a particular implementation in a feedlot fence structure.

Furthermore, in the preferred embodiment of the invention, the feedlot fence crossbar-embedded RFID antenna (207) is physically attached to or incorporated into a feedlot fence cross bar (e.g. 209). In the particular embodiment of the feedlot fence structure (200) as shown in FIG. 2, the feedlot fence crossbar-embedded RFID antenna (207) is physically attached to a middle feedlot fence crossbar (209). In another embodiment of the invention, the feedlot fence crossbar-embedded RFID antenna (207) may instead be attached to an upper feedlot fence crossbar (213) or a lower feedlot fence crossbar (203).

Moreover, in the preferred embodiment of the invention, the feedlot fence structure (200), which is located near a livestock feeder (201), typically comprises a first vertical fence support (215), a second vertical fence support (211), and one or more feedlot fence crossbars (203, 209, 213), wherein at least one feedlot fence crossbar is attached to or incorporated into the feedlot fence crossbar-embedded RFID antenna (207). In the feedlot fence structure (200) as shown in FIG. 2, there are three feedlot fence crossbars (203, 209, 213), which generally serve the function of preventing the livestock animals from going through or jumping over the feedlot fence structure (200).

In one or more embodiments of the invention, at least one feedlot fence crossbar-embedded RFID antenna is attached to or incorporated into at least one feedlot fence crossbar, wherein at least one feedlot fence crossbar-embedded RFID antenna defines and provides a custom-tuned RFID tag access range to a perimeter above or around the livestock feeder (201). In addition, in the embodiment of the invention as shown in FIG. 2, the feedlot fence structure (200) additionally includes one or more side fence bars (217, 205) to further contain livestock animals' sideways movement. In another embodiment of the invention, side fence bars (217, 205) may not be present.

Figure 3:
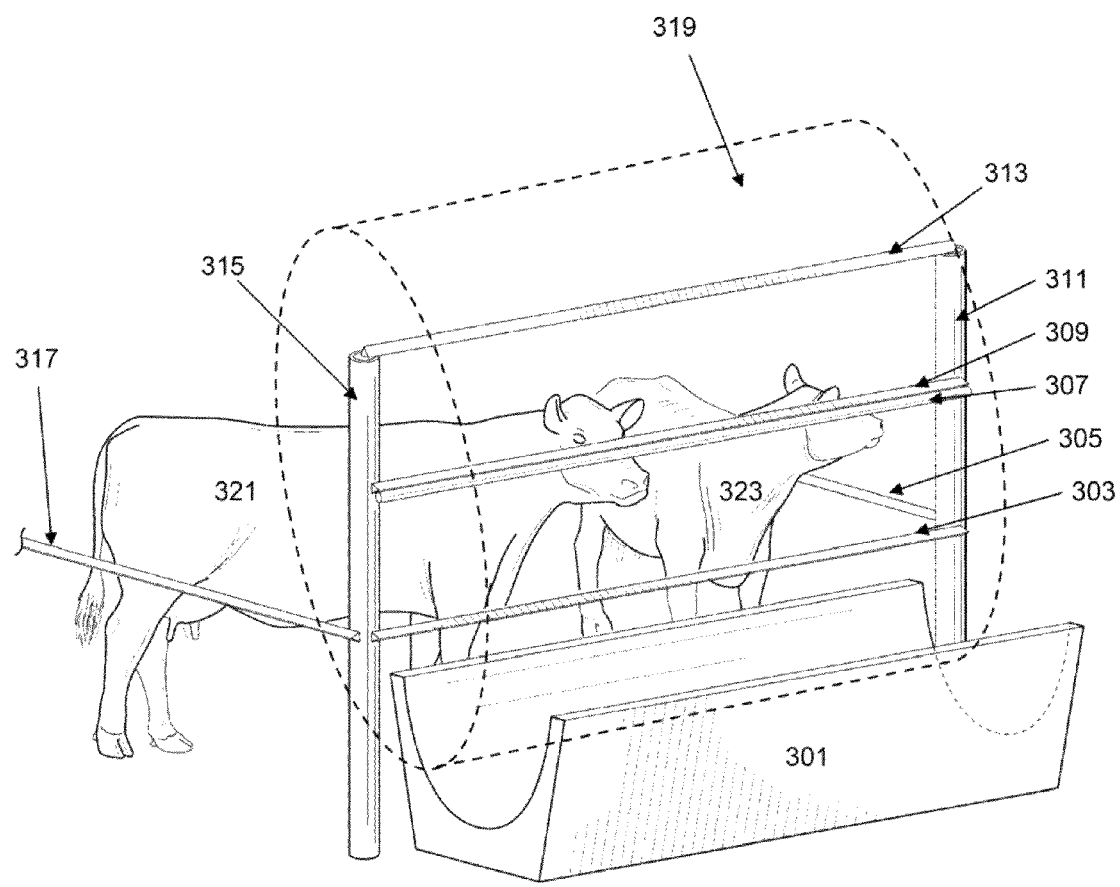
FIG. 3 shows a perspective view of a feedlot fence crossbar-embedded RFID antenna with a custom-tuned RFID tag access range for a livestock feeder, in accordance with an embodiment of the invention.

FIG. 3 shows a perspective view of a feedlot fence crossbar-embedded RFID antenna (307) in a feedlot fence structure (300) with a custom-tuned RFID tag access range (319) for a livestock feeder, in accordance with an embodiment of the invention. In a preferred embodiment of the invention, the feedlot fence crossbar-embedded RFID antenna (307) is a multiple-wavelength dipole antenna that can effectively produce the custom-tuned RFID tag access range (319) without requiring multiple half-wavelength dipole antennas within the feedlot fence crossbar-embedded RFID antenna (307). In another embodiment of the invention, the feedlot fence crossbar-embedded RFID antenna (307) is one or more discrete half-wavelength dipole antennas, which may produce higher signal-amplification efficiencies than the multiple-wavelength dipole antenna. In one example, the feedlot fence crossbar-embedded RFID antenna (307) is approximately 10~12 feet in length and 1~2 inches in diameter. In another example, the feedlot fence crossbar-embedded RFID antenna (307) exhibits other dimensions that are appropriately sized for a particular implementation in a feedlot fence structure.

Furthermore, in the preferred embodiment of the invention, the feedlot fence crossbar-embedded RFID antenna (307) is physically attached to or incorporated into a feedlot fence crossbar (e.g. 309). In the particular embodiment of the feedlot fence structure (300) as shown in FIG. 3, the feedlot fence crossbar-embedded RFID antenna (307) is physically attached to a middle feedlot fence crossbar (309). In another embodiment of the invention, the feedlot fence crossbar-embedded RFID antenna (307) may instead be attached to an upper feedlot fence crossbar (313) or a lower feedlot fence crossbar (303).

Moreover, in the preferred embodiment of the invention, the feedlot fence structure (300), which is located near a livestock feeder (301), typically comprises a first vertical fence support (315), a second vertical fence support (311), and one or more feedlot fence crossbars (303, 309, 313), wherein at least one feedlot fence crossbar is attached to or incorporated into the feedlot fence crossbar-embedded RFID antenna (307). In the feedlot fence structure (300) as shown in FIG. 3, there are three feedlot fence crossbars (303, 309, 313), which generally serve the function of preventing livestock animals (321, 323) from going through or jumping over the feedlot fence structure (300).

In one or more embodiments of the invention, at least one feedlot fence crossbar-embedded RFID antenna is attached to or incorporated into at least one feedlot fence crossbar, wherein at least one feedlot fence crossbar-embedded RFID antenna defines and provides a custom-tuned RFID tag access range (319) to a perimeter above or around the livestock feeder (301). In addition, in the embodiment of the invention as shown in FIG. 3, the feedlot fence structure (300) additionally includes one or more side fence bars (317, 305) to further contain livestock animals' sideways movement. In another embodiment of the invention, side fence bars (317, 305) may not be present.

As shown in FIG. 3, a key advantage of an embodiment of the present invention is that the uniquely-designed feedlot fence crossbar-embedded RFID antenna (307) is substantially more cost effective to manufacture and also to install at an onsite location (e.g. a feedlot fence structure (300)) than conventional devices and methods, which involve multiple RFID antennas around a livestock feeder or a separate high-rise stand that hangs one or more RFID antennas near the livestock feeder. For example, the conventional multiple antenna installation methods involve placing multiple RFID antennas underneath or inside the livestock feeder, or above the livestock feeder by using a separate high-rise stand. The cost of manufacturing and installing conventional multiple RFID antennas per livestock feeder is substantially more expensive than the cost of manufacturing and installing the uniquely-designed, single-piece feedlot fence crossbar-embedded RFID antenna (307) near the livestock feeder (301).

Furthermore, another advantage of an embodiment of the present invention is that the uniquely-designed feedlot fence crossbar-embedded RFID antenna (307) is substantially easier and less time-consuming to custom-tune RFID tag access ranges and install at an onsite location (e.g. a feedlot fence structure (300)) than conventional multiple RFID antennas underneath or inside the livestock feeder, or above the livestock feeder by using a separate high-rise stand. Because most livestock feeders, such as cattle feeders, have a feedlot fence structure with at least one feedlot fence crossbar near or above each livestock feeder, a farmer can easily attach the feedlot fence crossbar-embedded RFID antenna (307) to an existing feedlot fence crossbar. Preferably, the farmer can even adjust and custom-tune RFID tag access range (319) by adjusting the height of the feedlot fence crossbar (309) that incorporates the feedlot fence crossbar-embedded RFID antenna (307).

Figure 4:
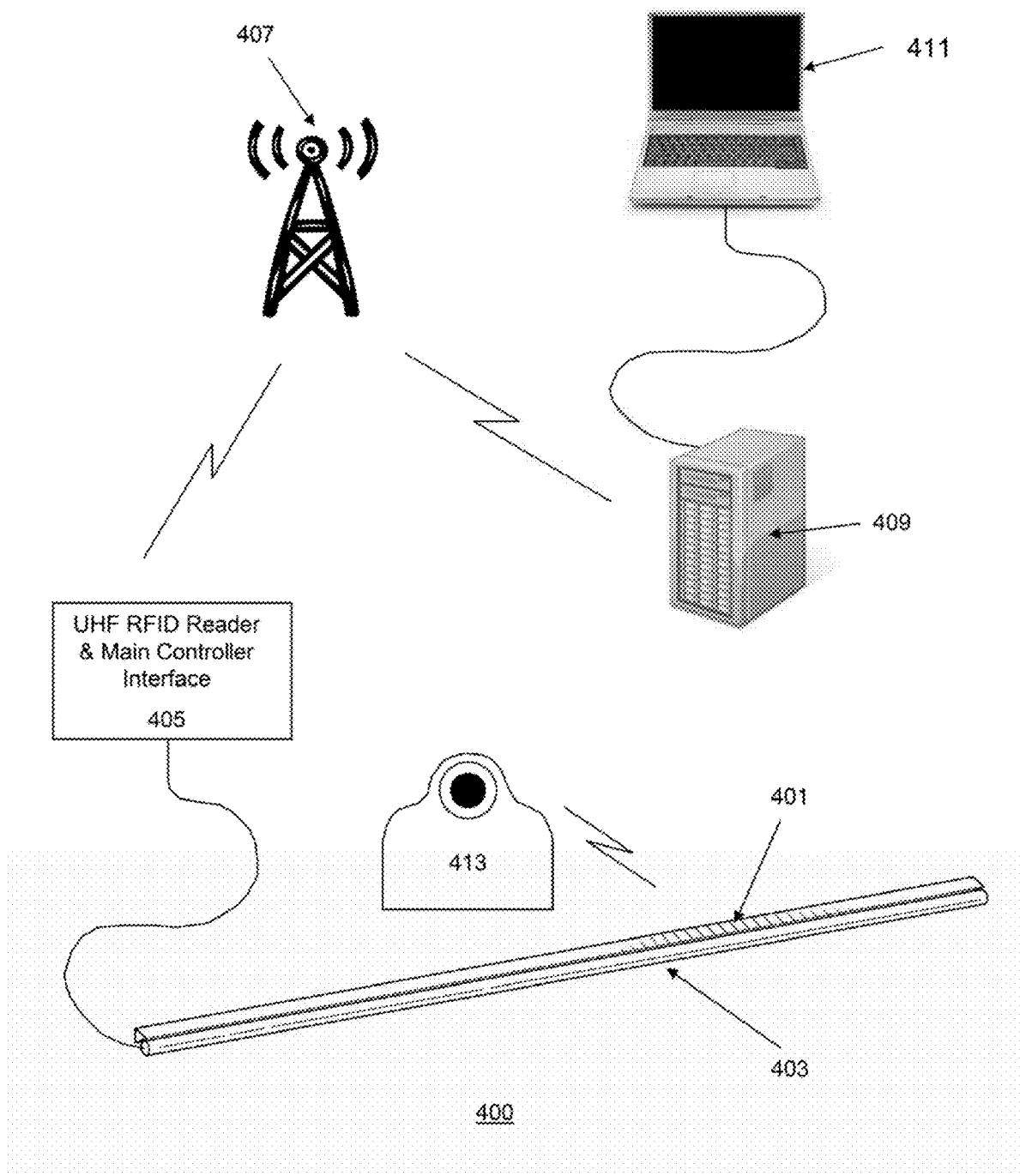
FIG. 4 shows a system diagram for an early alert system for livestock disease detection with a feedlot fence crossbar-embedded RFID antenna, in accordance with an embodiment of the invention.

FIG. 4 shows a system diagram (400) for an early alert system for livestock disease detection with a feedlot fence crossbar-embedded RFID antenna (403), which is attached to or incorporated into a feedlot fence crossbar (401), in accordance with an embodiment of the invention. In a preferred embodiment of the invention, the early alert system for livestock disease detection comprises a UHF RFID tag reader & main controller interface (405), a feedlot fence crossbar-embedded RFID antenna (403) that defines an activity measurement zone (AMZ) around a livestock feed, an RFID tag (413) operatively attached to an animal, a wireless transceiver (407) (e.g. a WiFi transceiver, a cellular base station, another wireless protocol transceiver, or a combination thereof), a computer server (409) configured to process, display, and/or store RFID tag-related information, and a computerized user interface (411) that operates or has access to an analytical program module to set, adjust, detect, and/or use an alert trigger point for alerting a user that the animal requires personal attention for further inspection and determination of its health. Furthermore, the early alert system may also utilize an email alert, a telephone call, and/or a text message to alert the user (e.g. a farmer) that the alert trigger point is reached for a potential livestock disease on the animal with the RFID tag (413).

In the preferred embodiment of the invention, the alert trigger point is reached if the animal's activity measurement zone (AMZ) entry count drops dramatically over a period of time, and/or is less than what is considered a healthy amount of activity to the AMZ. Furthermore, in the preferred embodiment of the invention, the analytical program module is an application software program, which receives information from the RFID tag (413) or transmits information to the RFID tag (413). This software program may be configured to be executed on a CPU and a memory unit of the computer server (409).

In one or more embodiments of the invention, the communication among the UHF RFID tag reader & main controller interface (405), the feedlot fence crossbar-embedded RFID antenna (403), the computer server (409), and the computerized user interface (411) may be implemented using at least some wired connections for device communications, instead of only utilizing wireless communications. Therefore, one or more embodiments of the invention may not require the wireless transceiver (e.g. 407), if the communication points between the UHF RFID tag reader & main controller interface (405) and the computer server (e.g. 409) are based on wired lines.

Furthermore, in one or more embodiments of the invention, the computerized user interface (411) may be embodied in a desktop or a laptop computer, which may also optionally integrate the functionality of a separate computer server (e.g. 409), thereby making the separate computer server (e.g. 409) unnecessary in their respective implementations.

Continuing with FIG. 4, in one or more embodiments of the invention, it may be desirable to also install an incentive device, such as a livestock feeder, inside or near an AMZ (e.g. 319 of FIG. 3), because the incentive device (e.g. the livestock feeder) motivates a farm animal to enter the AMZ (e.g. 319 of FIG. 3) frequently or periodically. Farm animals which are anemic and/or less active over a particular period of time may indicate that they are getting sick and/or require medical attention. A novel aspect of the early alert system and method for livestock disease detection is related to farm animals' general tendency to become more inactive if they are getting sick. Therefore, an animal's sudden or gradual drop in its activity level near an incentive (e.g. food, water, and etc.) can be a good indication of its deteriorating health. By utilizing the UHF RFID tag reader & main controller interface (405) with the feedlot fence crossbar-embedded RFID antenna (403), which is capable of simultaneous multiple RFID tag accesses on farm animals in a defined RFID tag access area (i.e. an AMZ defined by 319 in FIG. 3) with an incentive device (e.g. 301 of FIG. 3) inside or nearby, one or more embodiments of the present invention disclose unique and novel systems and methods that enable an early and proactive detection of a farm animal's onset of disease or sickness. One or more embodiments of the present invention may be particularly useful for alerting a farmer for a potentially-infectious disease on a particular farm animal attached with an RFID tag (e.g. 413) based on its reduced activity levels to the activity measurement zone (AMZ).

Figure 5:
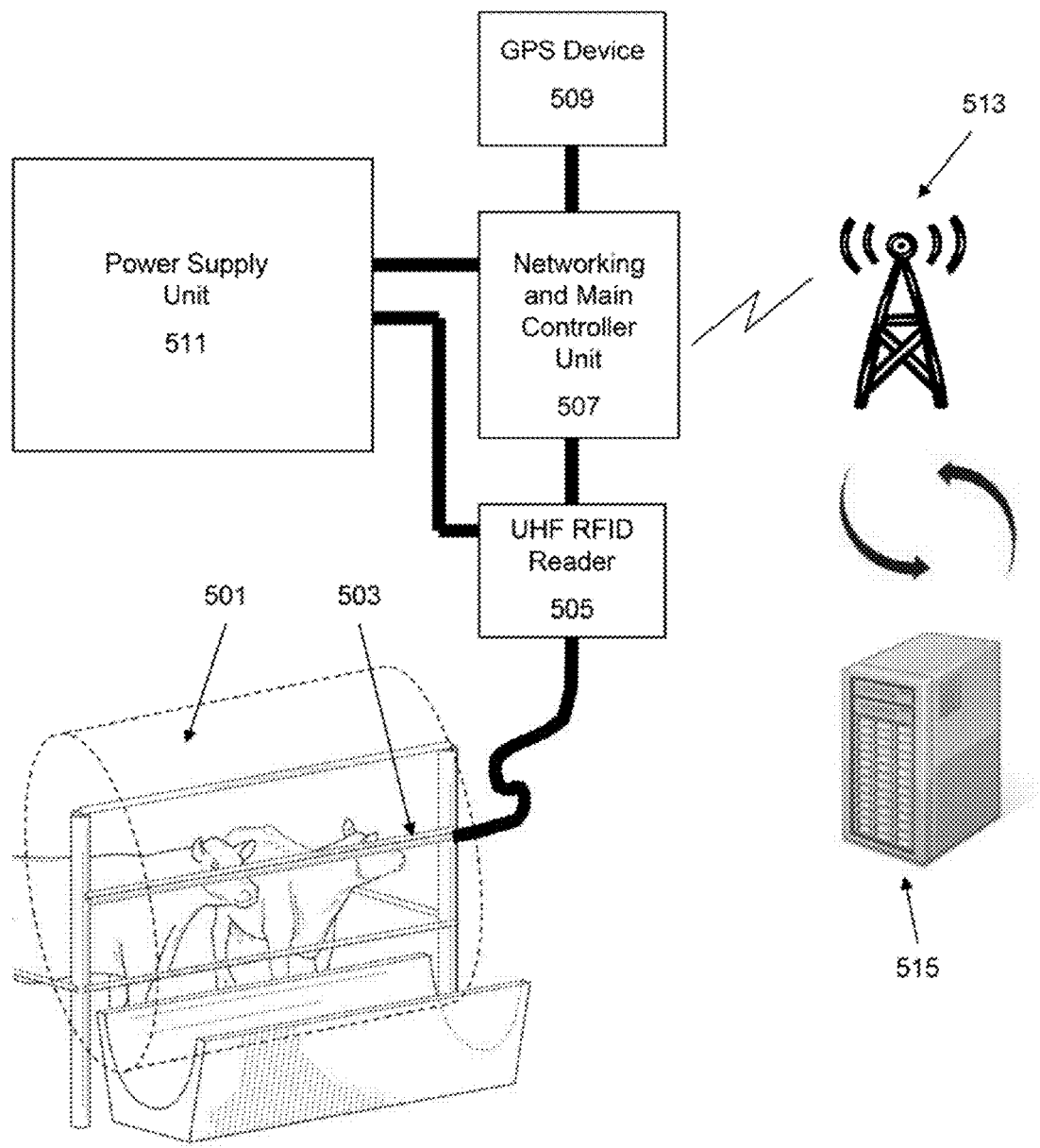
FIG. 5 shows a system diagram for an early alert system for livestock disease detection with a feedlot fence crossbar-embedded RFID antenna, which is installed for a livestock feeder, in accordance with an embodiment of the invention.

FIG. 5 shows another system diagram (500) for an early alert system for livestock disease detection with a feedlot fence crossbar-embedded RFID antenna (503), which is installed for a livestock feeder, in accordance with an embodiment of the invention. In a preferred embodiment of the invention, the early alert system for livestock disease detection comprises a power supply unit (511), a networking and main controller unit (507), a UHF RFID tag reader (505), a feedlot fence crossbar-embedded RFID antenna (503) that forms an activity measurement zone (AMZ) (501) near a livestock feeder, a cellular or satellite communication network (513), and a database and web interface system residing in a computer server (515). Furthermore, the early alert system may also include a GPD device (509).

As shown in FIG. 5, in one embodiment of the invention, the power supply unit (511) may be operatively connected to an electrical outlet and/or an alternative energy source to supply and regulate electrical power to some of the components (e.g. 503, 505, 507, 509) in the early alert system. Furthermore, in one embodiment of the invention, the networking and main controller unit (507) comprises an interface controller, a main processor, a wireless modem, and an Ethernet controller. The networking and main controller unit (507) is designed to manage, track, filter, and report animal activities in the activity measurement zone (AMZ) by communicating instructions and RFID tag-related data with the UHF RFID tag reader (505), the feedlot fence crossbar-embedded RFID antenna (503), and the database and web interface system residing in the computer server (515).

In a preferred embodiment of the invention, at least some portions of the networking and main controller unit (507) is a portable unit capable of communicating with the UHF RFID tag reader (505), the feedlot fence crossbar-embedded RFID antenna (503), and the database and web interface system residing in the computer server (515) via a local area network (LAN), a cellular or satellite communication network (e.g. 513), an Internet connection, and/or a wired or wireless data connection using the Ethernet controller, the wireless modem, and the interface controller of the networking and main controller unit (507). In a preferred embodiment of the invention, the portable unit utilizes RS232 or RS485 communication interfaces to communicate with at least some parts of the early alert system. Furthermore, the GPS device (509) may assist identifying the current location of the portable unit or another device unit relative to the UHF RFID tag reader (505), the feedlot fence crossbar-embedded RFID antenna (503), and the database and web interface system residing in the computer server (515). In another embodiment of the invention, the networking and main controller unit (507) may be entirely a fixed unit attached to one particular location, such as a wall or a device system tower.

Furthermore, some features of the networking and main controller unit (507) which may be part of the portable unit include, but are not limited to, an application program executed on a microprocessor to retrieve animal activity-related RFID tag data periodically, and a user interface (e.g. a keypad, a keyboard, buttons, switches, and etc. on the portable unit) to request transmission of instructions to the UHF RFID tag reader (505) and the feedlot fence crossbar-embedded RFID antenna (503), or to request data from the UHF RFID tag reader (505) and the feedlot fence crossbar-embedded RFID antenna (503).

Furthermore, in one embodiment of the invention, the portable unit associated with the networking and main controller unit (507) may also control the power supply unit (511) for power supply adjustments, and also control data transmission to or reception from the database and web interface system residing in the computer server (515) for operation of the early alert system for livestock disease detection.

Continuing with FIG. 5, in a preferred embodiment of the invention, the database and web interface system residing in the computer server (515) comprises a data file server and a web server, which may be separate computer server units or a combined integrated computer server unit. The data file server may function as a network attached storage (NAS) that stores and updates animal-specific RFID tag data associated with an activity measurement zone (AMZ) as well as an analytical program module configured to set, adjust, detect, and/or use an alert trigger point for alerting a user that a particular animal requires personal attention for further medical inspection if an AMZ count for the animal over a period of time drops below the alert trigger point, as previously described for other figures. Furthermore, the web server may store and operate an Internet application module to provide a user interface to control, manage, and/or visualize data or control interfaces associated with the early alert system for livestock disease detection. This user interface may be accessed by a computer terminal, a mobile device, or a networking and main controller system.

In one embodiment of the invention, the analytical program module may be entirely resident on the database and web interface system and execute its program routines in a CPU and a memory unit of the computer server (515) operating the database and web interface systems. In this embodiment of the invention, results from the analytical program module may be communicated with the networking and main controller unit (507) via a cellular or satellite communication network (513) or another data network. In another embodiment of the invention, some portions of the analytical program module may also be executed on a main processor and a memory unit of the networking and main controller unit (507), while other portions of the analytical program module may be executed on a CPU and a memory unit of the computer server (515) operating the database and web interface system.

Figure 6:
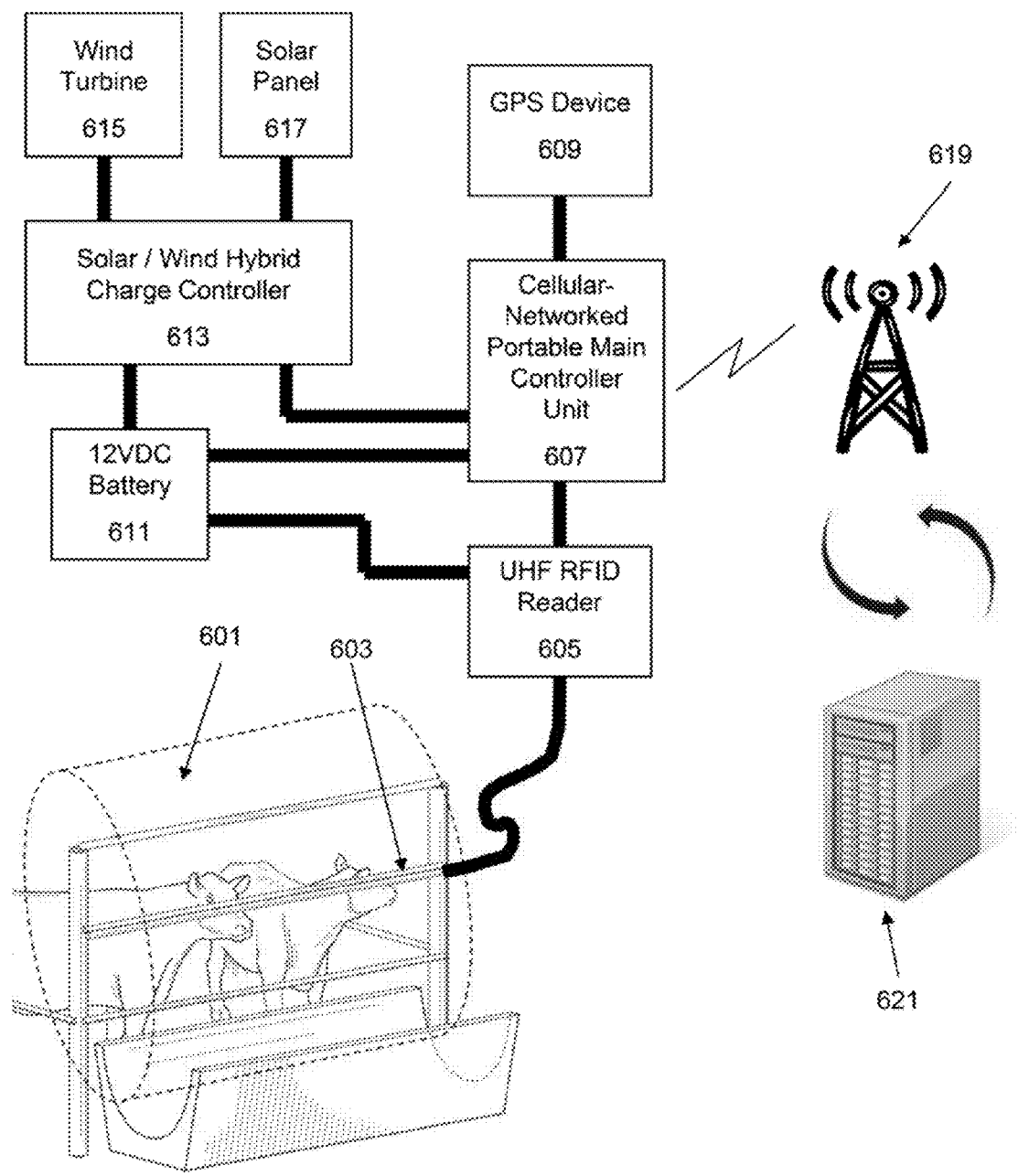
FIG. 6 shows a system diagram for an early alert system for livestock disease detection with a feedlot fence crossbar-embedded RFID antenna, which is installed for a livestock feeder and powered by alternative energy sources, in accordance with an embodiment of the invention.

FIG. 6 shows a system diagram (600) for an early alert system for livestock disease detection with a feedlot fence crossbar-embedded RFID antenna (603), which is installed for a livestock feeder and powered by alternative energy sources, in accordance with an embodiment of the invention. In a preferred embodiment of the invention, the early alert system for livestock disease detection powered by alternative energy sources comprises a "power source system" (i.e. 615, 617, 613, 611), a "networking and main controller system" (i.e. 607, 609), an "RFID scanning system" (i.e. 605, 603, 601), a cellular communication network (619), and a database and web interface system server (621). In the preferred embodiment of the invention, the power source system includes a wind turbine (615) and a solar panel (617), which are operatively connected to a solar/wind hybrid controller (613). The wind turbine (615) and the solar panel (617) are alternative energy sources that provide electrical currents and voltages to the solar/wind hybrid charge controller (613), which in turn converts, regulates, and controls the incoming electrical currents and voltages from the alternative energy sources for charging a rechargeable battery unit (611).

In the preferred embodiment of the invention, the wind turbine (615) provides an alternate current (AC) and intermittent electrical energy to the solar/wind hybrid charge controller (613), while the solar panel (617) provides a direct current (DC) and intermittent electrical energy to the solar/wind hybrid charge controller (613). In one embodiment of the invention, an important function of the hybrid charge controller (613) is converting, regulating, and controlling these incoming electrical currents and voltages into an optimized form of electrical energy for charging the rechargeable battery unit (611). In one embodiment of the invention, the solar/wind hybrid charge controller (613) converts any incoming alternate current (AC) into direct current (DC) and also converts voltage levels to be compatible to that of the rechargeable battery unit (611). The solar/wind hybrid charge controller (613) also protects the rechargeable battery unit (611) and other electrical components from dangerous or undesirable voltage and current surges, which may occur while receiving electrical energy from the alternative energy sources (e.g. 615, 617). In one example of an embodiment of the invention, the rechargeable battery unit (611) operates at 12 VDC with a maximum operating current of 200 amps. In one embodiment of the invention, the wind turbine (615) has a maximum power generation capacity of 400 Watts, and the solar panel (617) has a maximum power generation capacity of 60 Watts.

Continuing with FIG. 6, in the preferred embodiment of the invention, the rechargeable battery unit (611) powers at least some of the components in the RFID scanning system (i.e. 605, 603, 601) and optionally at least a portion of the networking and main controller system (i.e. 607, 609). In one embodiment of the invention, the RFID scanning system comprises a UHF RFID tag reader (605) operatively connected to a feedlot fence crossbar-embedded RFID antenna (603), which may monitor and track animal activities in an activity measurement zone (AMZ) (601) by tracking an RFID tag attached to an animal, if the animal enters the AMZ (601), typically located near an incentive device such as a livestock feeder.

Furthermore, in one embodiment of the invention, the networking and main controller system comprises a GPS device (609) operatively connected to a cellular-networked portable main controller unit (607). The GPS device (609) may be an integrated unit within the cellular-networked portable main controller unit (607) in one embodiment of the invention. Alternatively, the GPS device (609) may be a separate unit operatively connected to the cellular-networked portable main controller unit (607) in another embodiment of the invention. In a preferred embodiment of the invention, the cellular-networked portable main controller unit (607) includes a data interface controller which may utilize RS 232 or RS485 protocols, a main processor, a wireless modem, and an Ethernet controller. In the preferred embodiment of the invention, the cellular-networked portable main controller unit (607) also includes a memory unit to execute application programs and an internal battery to power the components in the cellular-networked portable main controller unit (607). The networking and main controller system (i.e. 607, 609) is designed to manage, track, filter, and report animal activities in the activity measurement zone (AMZ) (601) by communicating instructions and RFID tag-related data with the RFID scanning system (i.e. 605, 603, 601) and the database and web interface system server (621).

In a preferred embodiment of the invention, the cellular-networked portable main controller unit (607) is a portable unit capable of communicating with other parts of the early alert system for livestock disease detection. The cellular-networked portable main controller unit (607) may accomplish communication with other parts of the early alert system via a local area network (LAN), a cellular communication network (e.g. 619), an Internet connection, and/or a wired or wireless data connection by using an Ethernet controller, a wireless modem, and an interface controller within the networking and main controller system (i.e. 607, 609). In addition, the GPS device (609) may assist identifying the current location of the cellular-networked portable main controller unit (607) or another device unit relative to other parts of the early alert system.

Furthermore, some features of the cellular-networked portable main controller unit (607) include, but are not limited to, an application program executed on its microprocessor to retrieve animal activity-related RFID tag data periodically, and a user interface (e.g. a keypad, a keyboard, buttons, switches, and etc. on the portable unit) to request transmission of instructions to the RFID scanning system (i.e. 605, 603, 601), or to request data from the RFID scanning system (i.e. 605, 603, 601). Moreover, in one embodiment of the invention, the cellular-networked portable main controller unit (607) may also control the power source system (i.e. 615, 617, 613, 611) for power supply adjustments, and also control data transmission to or reception from the database and web interface system server (i.e. 621) for operation of the early alert system for livestock disease detection.

Continuing with FIG. 6, in a preferred embodiment of the invention, the database and web interface system server (621) carries the functionality of a data file server and a web server as a single computer server unit. In another embodiment of the invention, the data file server and the web server may be separate computer server units. The database and web interface system server (621) may function as a network attached storage (NAS) that stores and updates animal-specific RFID tag data associated with an activity measurement zone (AMZ) (601), while also being capable of executing an analytical program module configured to set, adjust, detect, and/or use an alert trigger point for alerting a user that a particular animal requires personal attention for further medical inspection if an AMZ count for the animal over a period of time drops below the alert trigger point, as previously described for other figures. Furthermore, the database and web interface system server (621) may store and operate an Internet application module to provide a user interface to control, manage, and/or visualize data or control interfaces associated with the early alert system for livestock disease detection. This user interface may be accessed by a computer terminal, a mobile device, or a cellular-networked portable main controller unit (607).

In one embodiment of the invention, the analytical program module may be entirely resident on the database and web interface system server (621) and execute its program routines in a CPU and a memory unit of the database and web interface system server (621). In this embodiment of the invention, results from the analytical program module may be communicated with the cellular-networked portable main controller unit (607) via a cellular communication network (619) or another data network. In another embodiment of the invention, some portions of the analytical program module may also be executed on a main processor and a memory unit of the cellular-networked portable main controller unit (607), while other portions of the analytical program module may be executed on a CPU and a memory unit of the database and web interface system server (621).

Figure 7:
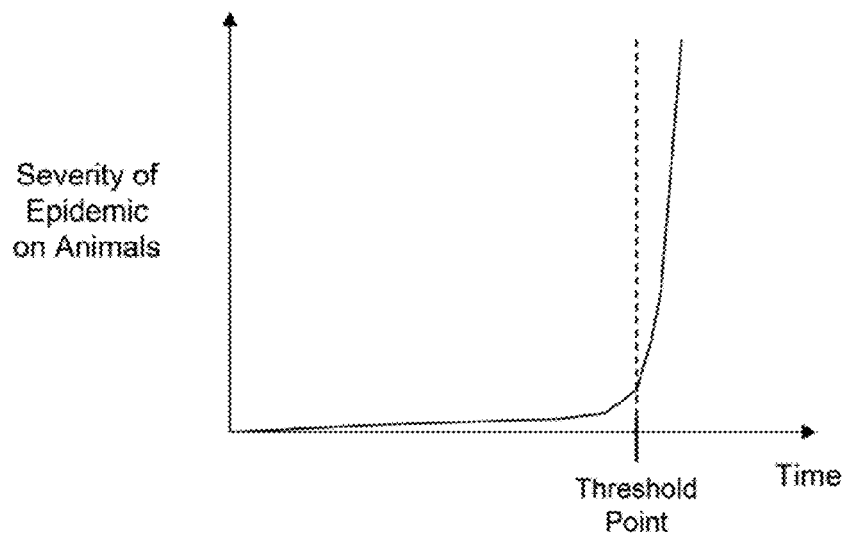
FIG. 7 shows an example of characteristics of an epidemic among animals in a livestock housing.

The importance of early detection of an infectious livestock disease is illustrated in FIG. 7. FIG. 7 shows an example (700) of characteristics of an epidemic among animals in a livestock housing, in accordance with an embodiment of the invention. In this example, the severity of epidemic on animals is graphed against time after the start of an infection on a first infected animal. The epidemic starts with a single infected animal, but begins to spread exponentially as the number of infected animals multiplies in the livestock housing. A "threshold point" relative to the progression of time is shown to illustrate that there comes a point of "no return," or a starting point for a very difficult epidemic containment in the livestock housing, if the epidemic is accidentally left unnoticed and/or untreated.

Therefore, the novel early alert system and method for livestock disease detection as shown in various embodiments of the present invention may become a very helpful tool for farmers to detect, control, and treat any outbreak of infectious diseases earlier and more accurately than manual inspection of the farm animals. The novel early alert system and method for livestock disease detection may be especially useful in containing potential damages and preventing further outbreak of an infectious disease, if an early alert for a potential outbreak of the infectious disease is given to a farmer well before the threshold point of "no return," as shown in FIG. 7.

Figure 8:
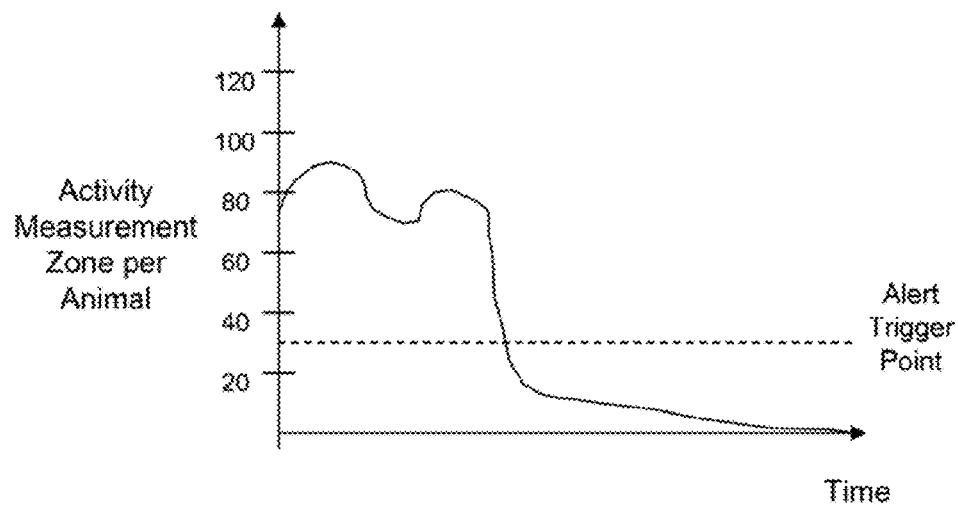
FIG. 8 shows an example of an alert trigger point for livestock disease detection, in accordance with an embodiment of the invention.

FIG. 8 shows an example (800) of an alert trigger point for livestock disease detection, in accordance with an embodiment of the invention. This example shows an activity measurement zone per animal plotted against a progression of time, as shown by the graph. In this particular example, an animal with an RFID tag is tracked for its entry and exit into an activity measurement zone (AMZ) over a period of one week. For the first few days, the animal showed a normal level of activity in and out of the AMZ (e.g. 70~90 entries into the AMZ). Then, the animal's activity level in and out of the AMZ suddenly drops to an alarming level, which is exemplified by crossing of the "alert trigger point" when the animal's activity into the AMZ falls below 30 entries per day.

In a preferred embodiment of the invention, the early alert system and method for livestock disease detection keeps track of activity levels of each animal with an RFID tag, and an animal with an AMZ-related activity level falling below the alert trigger point is flagged as a potential health problem worthy of a farmer's attention. It should be noted that reaching the alert trigger point does not necessarily mean that the animal in question is sick. For example, the alert trigger point may be reached as a result of an equipment-related false alarm, or unusual circumstances without any outbreak of a disease. However, a sudden or unusual drop in an animal's AMZ-related activity level strongly indicates that a health problem likely caused the animal's reduced activity levels, and a system-level alert for a closer personal inspection of the animal in question is justified for proactive prevention, detection, and management of livestock diseases.

In the preferred embodiment of the invention, the tracking of activity levels of each animal with an RFID tag is coordinated and managed by an analytical program module, which is configured to set, adjust, detect, and/or use an alert trigger point for alerting a user that a particular animal requires personal attention for further inspection and determination of its health.

In one exemplary use of the analytical program module, the analytical program may use statistical methods to calculate and determine what is a good alert trigger point. In another exemplary use of the analytical program module, the analytical program may allow a user (e.g. a farmer) to manually choose an alert trigger point based on a cutoff value for activity levels per day, week, or another defined period of time. In one or more embodiments of the invention, the analytical program module may reside in a computer server (e.g. 409 in FIG. 4), a desktop computer, and/or a laptop computer.

If the alert trigger point is reached for a particular animal, as shown in FIG. 8, the early alert system may alert the user via a computerized user interface (e.g. 411 in FIG. 4). Furthermore, the early alert system may also utilize an email alert, a telephone call, and/or a text message to alert the user proactively that the alert trigger point is reached for further personal attention to the particular animal. For example, in one embodiment of the invention, the early alert system may generate the email alert first, and then also proceed to the telephone call-based alert if necessary.

Figures 9, 10A, 10B:
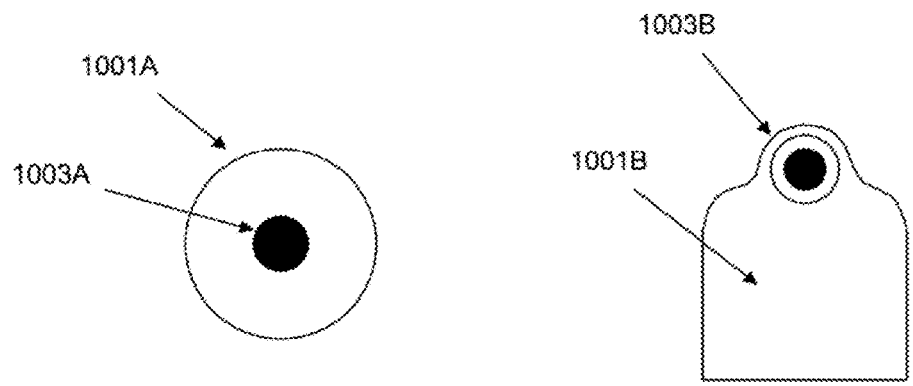
FIG. 9 shows an example of information stored in a computer server, another data storage, and/or an RFID tag attachable to an animal, in accordance with an embodiment of the invention.
FIG. 10A shows an example of an RFID tag attachable to an animal, in accordance with an embodiment of the invention.
FIG. 10B shows another example of an RFID tag attachable to an animal, in accordance with an embodiment of the invention.

FIG. 9 shows an example of information (900) stored in a computer server, another data storage, and/or an RFID tag attachable to an animal, in accordance with an embodiment of the invention. In a preferred embodiment of the invention, an RFID tag attachable to a particular animal stores a unique tag identification code (901) designed to identify the particular animal among a plurality of animals. The unique tag identification code (901) for the particular animal is also typically associated with other pieces of information, such as a type/grade of the animal (903), date of birth (905), gender (907), owner (909), and vaccine records (911) for the particular animal. In addition, the RFID tag, a computer server, and an analytical program module executed on the computer server may also keep records of castration because the completion of castration may impact a particular animal's behavior.

Furthermore, in one or more embodiments of the invention, an activity measurement zone (AMZ) count (913) is also tracked, updated, and associated with the particular animal identified by the unique tag identification code (901). In one embodiment of the invention, tracking and updating the AMZ count (913) may be a task of an analytical program module, which is also responsible for setting, adjusting, detecting, and/or using an alert trigger point for alerting a user that the particular animal requires personal attention for further inspection and determination of its health. In another embodiment of the invention, tracking and updating the AMZ count (913) may be a task of another software and/or hardware module which communicates with the analytical program module. In one or more embodiments of the invention, the AMZ count (913) may be incremented by one for each entry of the particular animal into the AMZ. In addition, the AMZ count (913) may be periodically reset to an initialization value on a daily, weekly, or another period-defined basis, depending on a particular embodiment of the invention. In the preferred embodiment of the invention, if the AMZ count (913) within a particular period (e.g. daily, weekly, and etc.) for a particular animal (e.g. A00001) falls below the alert trigger point, then the user is alerted via a user display terminal, a phone call, an email alert, and/or a text message.

Continuing with FIG. 9, information (900) stored in an RFID tag attachable to an animal may also include other information (915) not shown in FIG. 9, such as location information associated with the RFID tag (i.e. based on GPS coordinates, cellular base station identification number, and etc.). In a preferred embodiment of the invention, the RFID tag per animal may be initialized with a fixed set of information, such as a unique tag identification code (901), a type/grade of the animal (903), date of birth (905), gender (907), and owner (909), while other pieces of information such as vaccine records (911) and AMZ counts (913) may be periodically or continuously updated throughout the lifetime of a particular animal. Furthermore, some or all pieces of information (900) can be read from or written to the RFID tag periodically or continuously throughout the lifetime of the particular animal for use by the analytical program module and/or other relevant modules, devices, and apparatuses to enable the early alert system for livestock disease detection.

An example of information read from or written to a particular RFID tag attached to a particular farm animal may include, but are not limited to, a tag ID (901), an animal type (903), date of birth (905), gender (907), owner (909), vaccine records (911), AMZ count (913), and/or other information (915), as illustrated by FIG. 9, which shows an example of information associated with an RFID tag attached to a farm animal. Alternatively, at least some of these information (e.g. a tag ID (901), an animal type (903), date of birth (905), gender (907), owner (909), vaccine records (911), AMZ count (913), and/or other information (915)) may be tracked and stored in a computer server in addition to or instead of being stored in an RFID tag.

FIG. 10A shows an example of a circular RFID tag (1000A) attachable to an animal in accordance with an embodiment of the invention. The circular RFID tag (1000A) is typically used for a smaller animal such as a pig. In a preferred embodiment of the invention, the circular RFID tag (1000A) is a battery-less (i.e. without a battery) "passive" tag, which comprises a non-volatile memory unit and an RFID antenna encapsulated by a weather-resistant covering (1001A). In the preferred embodiment of the invention, the circular RFID tag (1000A) has a diameter of 3.5 centimeters. The RFID antenna in the circular RFID tag (1000A) is configured to receive an electromagnetic signal from an RFID tag reader to energize the non-volatile memory unit inside the circular RFID tag (1000A) to transmit information from or send information to the non-volatile memory unit. In another embodiment of the invention, the circular RFID tag (1000A) may be a battery-powered "active" tag.

In the preferred embodiment of the invention, the circular RFID tag (1000A) also has an attachment pin mechanism (1003A) to enable a secure attachment of the circular RFID tag (1000A) to an ear or another body part of an animal. Furthermore, the weather-resistant covering (1001A) is generally made of sturdy plastic, rubber, and/or other synthetic materials which are non-poisonous for use with edible livestock.

FIG. 10B shows an example of a rectangular RFID tag (1000B) attachable to an animal in accordance with an embodiment of the invention. The rectangular RFID tag (1000B) can be used in a variety of animals, but most notably, cattle. In a preferred embodiment of the invention, the rectangular RFID tag (1000B) is a battery-less "passive" tag, which comprises a non-volatile memory unit and an RFID antenna encapsulated by a weather-resistant covering (1001B). The RFID antenna in the rectangular RFID tag (1000B) is configured to receive an electromagnetic signal from an RFID tag reader to energize the non-volatile memory unit inside the rectangular RFID tag (1000B) to transmit information from or send information to the non-volatile memory unit. In another embodiment of the invention, the rectangular RFID tag (1000B) may be a battery-powered "active" tag.

In the preferred embodiment of the invention, the rectangular RFID tag (1000B) also has an attachment pin mechanism (1003B) to enable a secure attachment of the rectangular RFID tag (1000B) to an ear or another body part of an animal. Furthermore, the weather-resistant covering (1001B) is generally made of sturdy plastic, rubber, and/or other synthetic materials which are non-poisonous for use with edible livestock.

Figure 11:
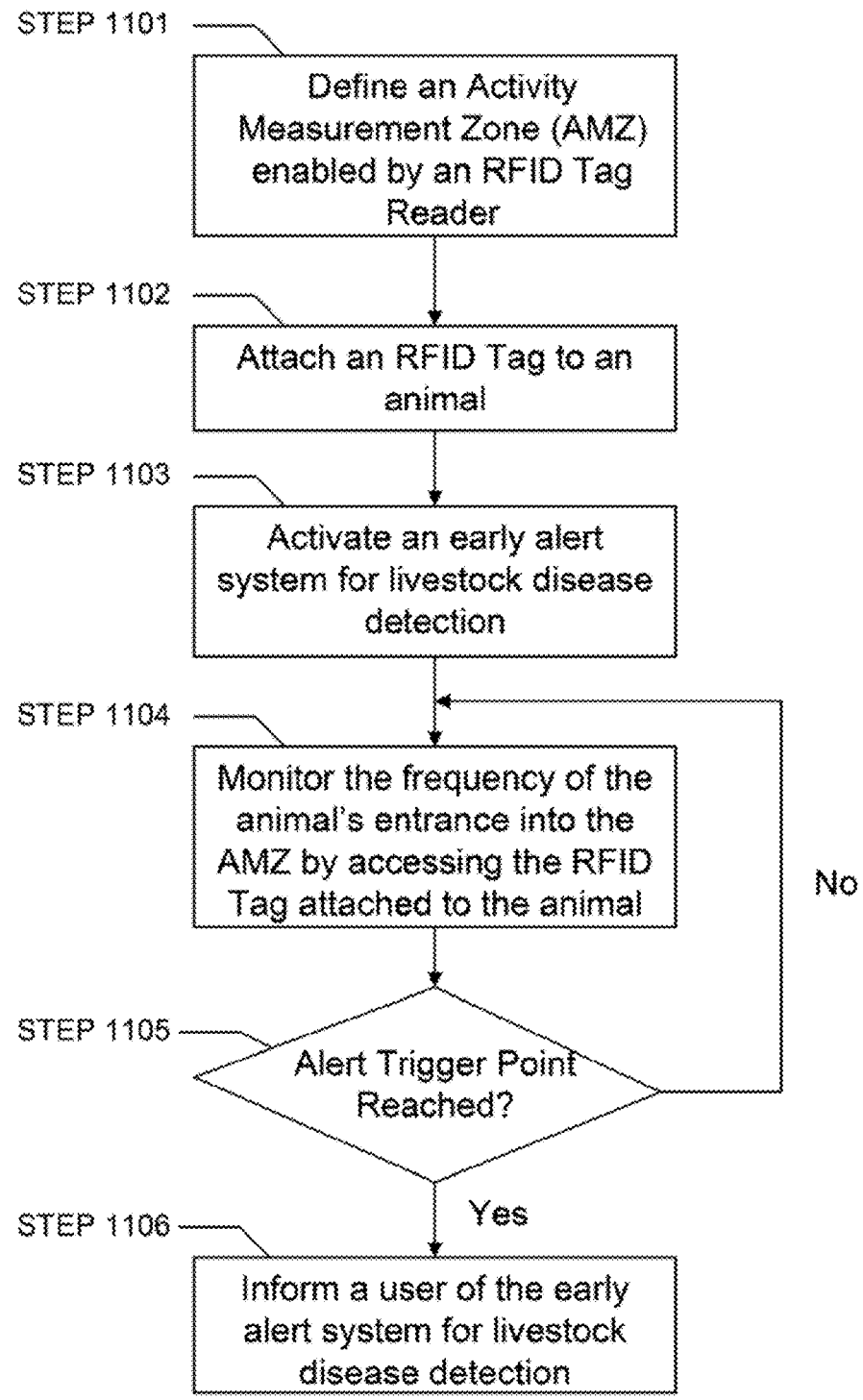
FIG. 11 shows a method of using an early alert system for livestock disease detection, in accordance with an embodiment of the invention.

FIG. 11 shows a method (1100) of using an early alert system for livestock disease detection in accordance with an embodiment of the invention. In a preferred embodiment of the invention, a user (e.g. a farmer) can define an activity measurement zone (AMZ) enabled by an RFID tag reader and/or an RFID antenna, as shown in STEP 1101. Then, the user may attach an RFID tag to an animal, as shown in STEP 1102. In one example, the RFID tag may be attached to an ear of the animal. In another example, the RFID tag may be attached to another body part of the animal. In most cases, data initialization of the RFID tag may be necessary prior to or during the attachment of the RFID tag to the animal. Then, the user can activate an early alert system for livestock disease detection, as shown in STEP 1103. In a preferred embodiment of the invention, the early alert system for livestock disease detection may resemble a system architecture shown in FIG. 4, FIG. 5, and/or FIG. 6. In another embodiment of the invention, the early alert system for livestock disease detection may incorporate at least partially wireline-based connections and/or other devices.

The early alert system for livestock disease detection, once activated, begins to monitor the frequency of the animal's entrance into the activity measurement zone (AMZ) by accessing the RFID tag attached to the animal, as shown in STEP 1104. In one embodiment of the invention, the early alert system tracks and counts the number of entrances to the AMZ per animal over a defined period of time by recognizing a unique tag identification code (e.g. 901) per each animal. The early alert system may store relevant data in a computer or a computer server. Furthermore, the RFID tag attached to the animal may also optionally store an AMZ entrance count, as previously shown by an AMZ count field (e.g. 913 in FIG. 9), if the RFID tag reader is configured to conduct a data field update function to store the AMZ entrance count for the RFID tag.

Continuing with FIG. 11, if an alert trigger point is reached because the AMZ count for a particular animal drops below the alert trigger point for a defined period of time, then the early alert system for livestock disease detection informs the user that personal attention is necessary to inspect the particular animal in question to determine its potential health problems, as shown in STEP 1106. On the other hand, if the alert trigger point is not reached during the monitoring phase of the animal's entrance into the AMZ, then the early alert system continues to monitor the frequency of the animal's entrance into the AMZ by accessing the RFID tag attached to the animal, as shown in STEPs 1104 and 1105.

Figure 12:
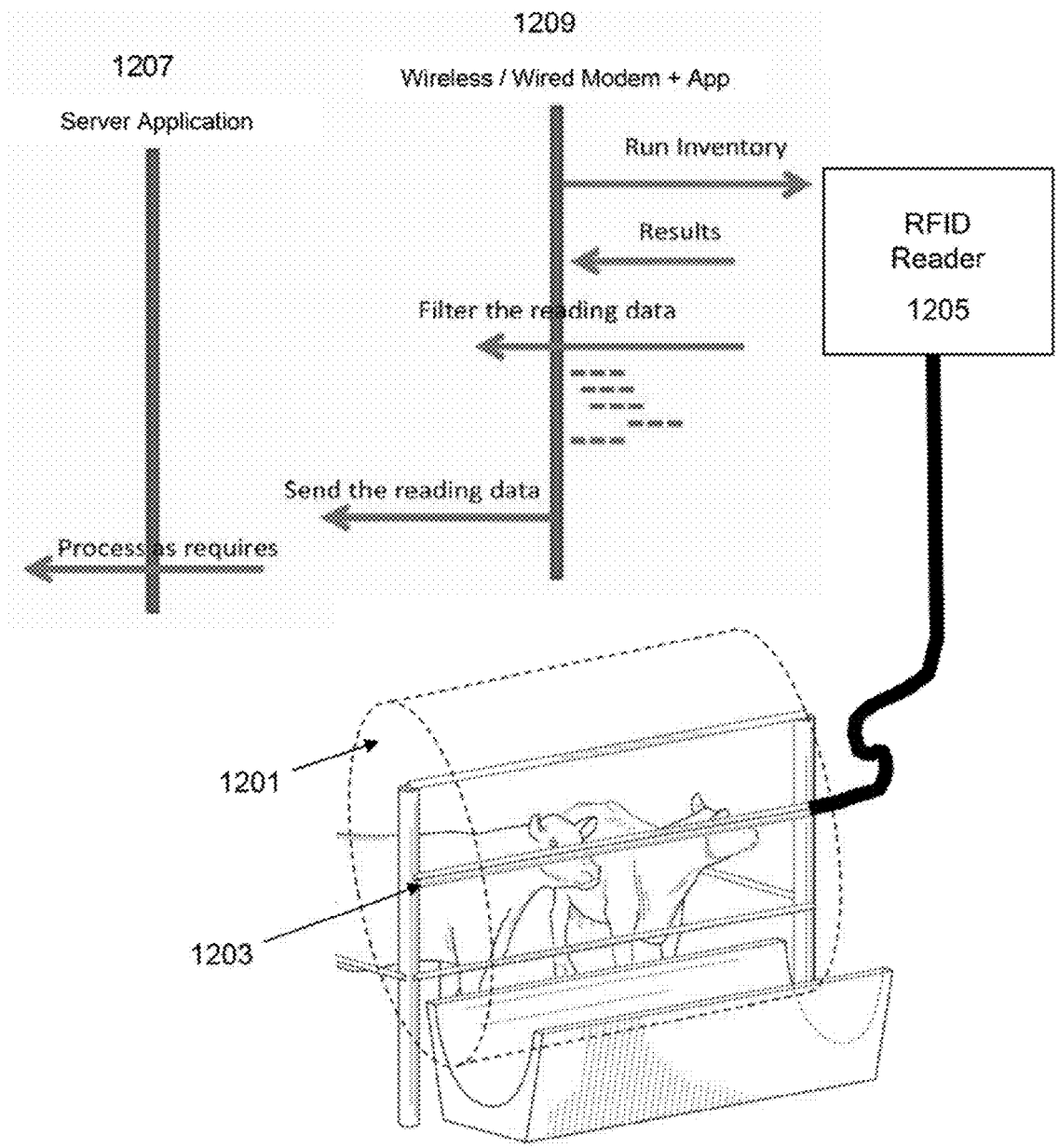
FIG. 12 shows an example of a system application flow diagram for an early alert system for livestock disease detection with a feedlot fence crossbar-embedded RFID antenna, in accordance with an embodiment of the invention.

FIG. 12 shows an example of a system application flow diagram (1200) for an early alert system for livestock disease detection with a feedlot fence crossbar-embedded RFID antenna (1203), in accordance with an embodiment of the invention. In a preferred embodiment of the invention, a portable or fixed main controller unit (e.g. 507 of FIG. 5), which is conceptually located at "Wireless and/or Wired Modem+App" layer (1209), may initiate a user's "run inventory" request to an RFID tag reader (1205) operatively connected to the feedlot fence crossbar-embedded RFID antenna (1203). This RFID antenna can define an activity measurement zone (AMZ) (1201) and access or modify information in an RFID tag attached to an animal, if the animal is within the AMZ (1201).

In one embodiment of the invention, the user's "run inventory" request is processed by the RFID tag reader (1205) and/or other components associated with the networking and main controller unit (e.g. 507 of FIG. 5), and resulting data are returned to the main controller unit at "Wireless and/or Wired Modem+App" layer (1209), as shown in FIG. 12. The resulting data can be filtered or refined by an application program executed on the networking and main controller unit, and the refined "reading data" can be transmitted to a "server application" layer (1207), which is located at a data file server and/or a web server in a database and web interface system (e.g. 515 of FIG. 5) via a cellular communication network.

Figure 13:
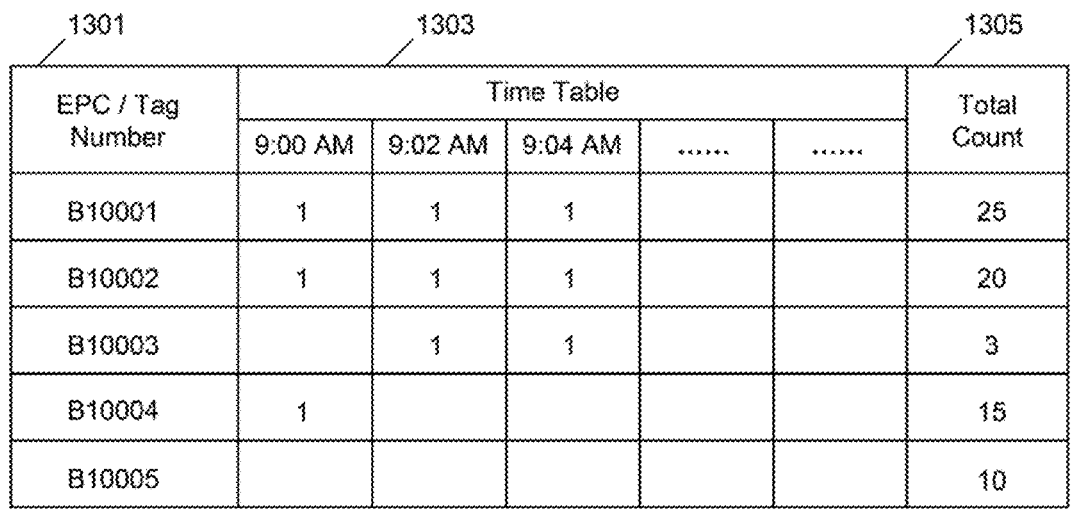
FIG. 13 shows an example of a report table format for an early alert system for livestock disease detection with a feedlot fence crossbar-embedded RFID antenna, in accordance with an embodiment of the invention.

FIG. 13 shows an example of a report table format (1300) for an early alert system for livestock disease detection with a feedlot fence crossbar-embedded RFID antenna, in accordance with an embodiment of the invention. In this embodiment of the invention, the report table format (1300) is generated, filtered, and/or refined by a networking and main controller system (e.g. 507 of FIG. 5), an RFID tag reader (e.g. 505 of FIG. 5), and/or the database and web interface system (e.g. 515 of FIG. 5). The report table format (1300) may contain a list of electronic product codes (EPC's) or unique RFID tag numbers (e.g. "B10001," "B10002," and etc.) in a first column (1301). The report table format (1300) may also contain a list of activity measurement zone (AMZ) accesses by a particular animal defined by a particular EPC or RFID tag number. Preferably, this list of AMZ accesses is further categorized by time, as shown in a second column (1303) in the report table format (1300). In a preferred embodiment of the invention, AMZ accesses for an animal attached with a specific RFID tag may be recorded periodically (e.g. every two minutes) and categorized in the second column (1303) accordingly. In addition, the report table format (1300) may also contain a total count of AMZ accesses by a particular animal, as shown in a third column (1305). As previously described in other figures, a sudden drop in a total count of AMZ accesses by a particular animal may indicate a potential health problem for that animal. An embodiment of the early alert system for livestock disease detection as described in the present invention is able to flag a particularly alarming drop in AMZ accesses by a potentially sick animal, and report to a user of the early alert system in the report table format (1300) as shown in FIG. 13, or in another method of alert, such as an email alert, a text alert, or a telephone call alert.

One or more embodiments of the early alert system with the feedlot fence crossbar-embedded RFID antenna and the method for livestock disease detection have been illustrated in FIGS. 1-13 and described above. The present invention provides several advantages over conventional solutions. For example, one advantage of an embodiment of the present invention is that the uniquely-designed feedlot fence crossbar-embedded RFID antenna is substantially more cost effective to manufacture and also to install at an onsite location (e.g. a feedlot fence structure) than conventional devices and methods, which involve multiple RFID antennas around a livestock feeder or a separate high-rise stand that hangs one or more RFID antennas near the livestock feeder. For example, the conventional multiple antenna installation methods involve placing multiple RFID antennas underneath or inside the livestock feeder, or above the livestock feeder by using a separate high-rise stand. The cost of manufacturing and installing conventional multiple RFID antennas per livestock feeder is substantially more expensive than the cost of manufacturing and installing the uniquely-designed, single-piece feedlot fence crossbar-embedded RFID antenna near the livestock feeder.

Furthermore, another advantage of an embodiment of the present invention is that the uniquely-designed feedlot fence crossbar-embedded RFID antenna is substantially easier and less time-consuming to custom-tune RFID tag access ranges and install at an onsite location (e.g. a feedlot fence structure) than conventional multiple RFID antennas underneath or inside the livestock feeder, or above the livestock feeder by using a separate high-rise stand. Because most livestock feeders, such as cattle feeders, have a feedlot fence structure with at least one feedlot fence crossbar near or above each livestock feeder, a farmer can easily attach the feedlot fence crossbar-embedded RFID antenna to an existing feedlot fence crossbar. Preferably, the farmer can even adjust and custom-tune RFID tag access range by adjusting the height of the feedlot fence crossbar that incorporates the feedlot fence crossbar-embedded RFID antenna.

In addition, the present invention also provides numerous advantages over conventional manual inspection of animals for determination of need for medical attention. For example, one or more embodiments of the present invention uniquely enable largely-automated early alert for a particular animal's alarming level of inactivity, which is likely to be a sign for sickness or deterioration of health. By defining an activity measurement zone (AMZ) inside or near an incentive device such as a livestock feeder, and by tracking and counting the particular animal's entry to or exit from the AMZ with an RFID tag reader and an RFID tag uniquely assigned to the particular animal, various embodiments of the present invention also make proactive and early alert possible for a potential livestock disease.

Furthermore, various embodiments of this early alert system can save farmers' unnecessary manual inspection time and manpower for a large group of animals and enable them to focus on particularly alarming levels of inactivity for certain animals flagged by the early alert system. Moreover, public health may be better protected with this early alert system for livestock disease detection in livestock farms, because the early alert system is likely to prevent the spread of an infectious disease on the livestock population well before reaching the threshold point of "no return" in exponential spread of the infectious disease, as discussed in FIG. 7.

In addition, in some embodiments of the invention, as shown and described for FIG. 6, powering the early alert system with alternative energy sources enables convenient installation of the early alert system for livestock disease detection in remote or rural areas (e.g. a remotely-located rural livestock farm), where access to conventional electrical power lines and outlets may be difficult, costly, or inconvenient. Furthermore, by utilizing alternative energy sources, this embodiment of the present invention is also environmentally-friendly and energy efficient.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An early alert system for livestock disease detection comprising:

a feedlot fence crossbar-embedded single-piece RFID antenna with an antenna dipole length equal to a length of a feedlot fence crossbar, wherein the feedlot fence crossbar encapsulates the feedlot fence crossbar-embedded single-piece RFID antenna longitudinally, with one end of the feedlot fence crossbar perpendicularly attached to a first vertical fence support bar and another end of the feedlot fence crossbar perpendicularly attached to a second vertical fence support bar, wherein the feedlot fence crossbar is also oriented parallel to and is located directly above a livestock feeder;

an activity measurement zone (AMZ) defined by an RFID signal projection from the feedlot fence crossbar-embedded single-piece RFID antenna operatively connected to an RFID tag reader, wherein the AMZ is further specified as a zone above or around the livestock feeder;

the livestock feeder located near or inside the AMZ to encourage an animal attached with an RFID tag to enter and exit the AMZ periodically or frequently;

the RFID tag reader configured to read from or write to the RFID tag attached to the animal if the animal is inside the AMZ defined by the RFID signal projection from the feedlot fence crossbar-embedded single-piece RFID antenna;

a portable or fixed main controller unit configured to control, request data from, or send data to one or more elements of the early alert system using a wireless connection, a physical connection, or both;

a power supply unit configured to supply and regulate electrical power to the feedlot fence crossbar-embedded single-piece RFID antenna, the RFID tag reader, and the portable or fixed main controller unit;

a computer server with a CPU and a memory unit operatively connected to the RFID tag reader and the portable or fixed main controller unit to receive information from or transmit information to the RFID tag attached to the animal; and an analytical program module that determines an alert trigger point in real-time by comparing an epidemic threshold point of no return for infectious disease spread in a livestock farm with an AMZ count for the animal over a period of time, wherein the alert trigger point is triggered for a livestock epidemic alert when a multiple number of sick animals tracked by the early alert system is approaching the epidemic threshold point of no return for infectious disease spread in the livestock farm, while the AMZ entry count for at least one animal continues to drop over the period of time, and wherein the analytical program module is executed on the CPU and the memory unit of the computer server.

2. The early alert system of claim 1, wherein the feedlot fence crossbar-embedded single-piece RFID antenna is a multiple-wavelength dipole antenna capable of providing RF signal amplification for a multiple number of RF signal wavelengths.

3. The early alert system of claim 1, further comprising a wireless transceiver operatively connecting the computer server, the portable or fixed main controller unit, and the RFID tag reader for data communication.

4. The early alert system of claim 1, further comprising a computerized user interface provided by a user display terminal to display information related to the RFID tag attached to the animal, including any alerts from the analytical program module.

5. The early alert system of claim 1, wherein the computer server is a desktop computer or a laptop computer, which integrates a user display terminal.

6. The early alert system of claim 1, wherein the RFID tag is a battery-less passive tag, and wherein the RFID tag comprises a non-volatile memory unit and an embedded RFID antenna unit.

7. The early alert system of claim 1, wherein the AMZ count is tracked and counted for the animal by the analytical program module executing on the CPU and the memory unit of the computer server.

8. The early alert system of claim 1, wherein the alert trigger point is either manually set by the user or statistically determined by the analytical program module executing on the CPU and the memory unit of the computer server.

9. The early alert system of claim 1, wherein the action of alerting the user for further medical inspection of the animal involves transmitting a phone alert, an email alert, a text message, or an alert display on a display terminal.

10. The early alert system of claim 1, wherein the RFID tag or the computer server stores at least some of information comprising a unique tag identification code for the animal, a type or grade of the animal, the animal's date of birth, gender, owner, and vaccine records.

11. The early alert system of claim 1, wherein the portable or fixed main controller unit comprises a display screen, a main controller unit specific-CPU, a main controller unit-specific memory unit, a keypad interface, a wireless modem, an Ethernet controller, an RS 232 interface controller, and a GPS receiver.

12. The early alert system of claim 1, wherein the power supply unit receives electrical power from a solar panel, a wind turbine, or another alternative energy source.

\* \* \* \* \*